United States Patent [19]

Schwierz

[11] Patent Number: 5,029,192

[45] Date of Patent: Jul. 2, 1991

[54] COMPUTER TOMOGRAPHY APPARATUS WITH DETECTOR WHICH IS ROTATABLE SEPARATELY FROM THE X-RAY SOURCE

[75] Inventor: Guenter Schwierz, Neunkirchen, Fed. Rep. of Germany

[73] Assignee: Siemens Aktiengesellschaft, Munich

[21] Appl. No.: 584,491

[22] Filed: Sep. 18, 1990

Related U.S. Application Data

[63] Continuation of Ser. No. 415,951, Sep. 2, 1989, abandoned.

[30] Foreign Application Priority Data

Nov. 9, 1988 [EP] European Pat. Off. ......... 88118681.1

[51] Int. Cl.$^5$ .......................... H05G 1/02; H05G 1/60
[52] U.S. Cl. ............................................. 378/4; 378/11; 378/14; 378/7; 378/19; 378/196
[58] Field of Search .................... 378/11, 14, 4, 7, 21, 378/116, 19, 39, 198, 196, 2, 116, 22, 15

[56] References Cited

U.S. PATENT DOCUMENTS

| | | | |
|---|---|---|---|
| 4,417,354 | 11/1983 | Pfeifer | 378/19 |
| 4,578,801 | 3/1986 | Oliver | 378/4 |
| 4,592,080 | 5/1986 | Rauch et al. | 378/19 |
| 4,677,554 | 6/1987 | Dobbs et al. | 378/19 |
| 4,769,827 | 9/1988 | Uno et al. | 378/19 |
| 4,853,946 | 8/1989 | Elliot et al. | 378/4 |

FOREIGN PATENT DOCUMENTS

| | | |
|---|---|---|
| 53-132985 | 11/1978 | Japan . |
| 1493596 | 11/1977 | United Kingdom . |
| 1522307 | 8/1978 | United Kingdom . |

Primary Examiner—Edward P. Westin
Assistant Examiner—Don Wong
Attorney, Agent, or Firm—Hill, Van Santen, Steadman & Simpson

[57] ABSTRACT

A computer tomography apparatus has an x-ray source which emits a fan-shaped x-ray beam which irradiates a slice of an examination subject. The x-ray source is rotatable around the examination subject to irradiate the slice from different angular directions in the plane of the slice. A row of detector elements is disposed to receive radiation attenuated by the examination subject as the x-ray source rotates around the patient. The radiation detector is disposed on a ring which is rotatable around the examination subject separately from the x-ray source. This permits to meet the conditions of the sampling theorem, applied to the projections with the focus as projection center, without increasing the number of defectors.

4 Claims, 1 Drawing Sheet

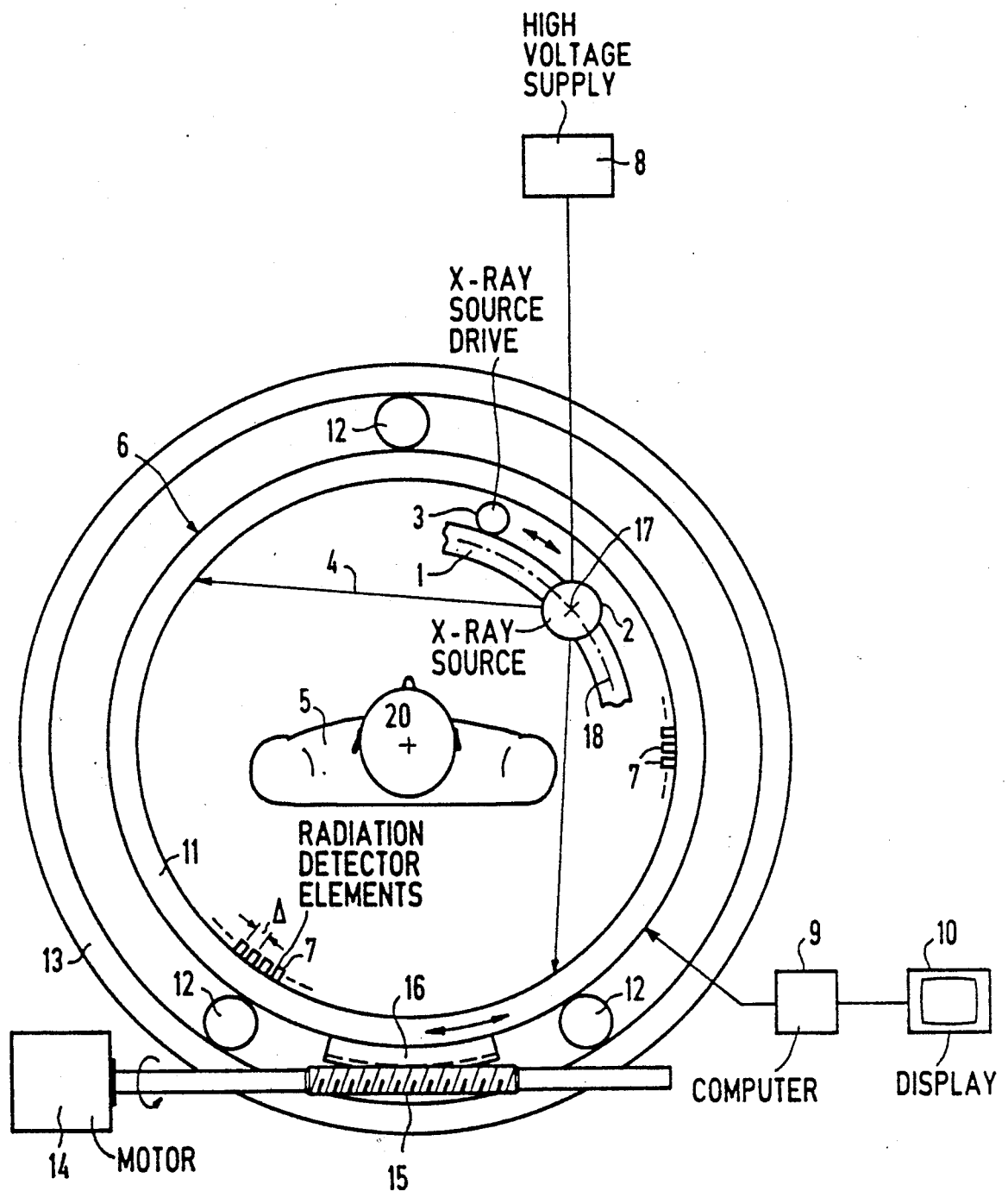

COMPUTER TOMOGRAPHY APPARATUS WITH DETECTOR WHICH IS ROTATABLE SEPARATELY FROM THE X-RAY SOURCE

This is a continuation of application Ser. No. 415,951, filed Sept. 2, 1989.

BACKGROUND OF THE INVENTION

1. Field of the Invention

The present invention is directed to computer tomography devices, and in particular to such devices having a radiation detector which is stationary or mutating.

2. Description of the Prior Art

In a Conventional computer tomography device, a source of penetrating radiation, such as an x-ray tube, emits a fan-shaped radiation beam. A row of detector elements is provided for detecting radiation attenuated by an examination subject disposed between the source of penetrating radiation and the detector row. The radiation source and/or detector are mounted on a live ring which is rotated around the examination subject, or the radiation source is electronically rotated, so that a slice of the examination subject is irradiated from a large number of different angular directions. A computer then constructs a viewable image from the outputs of the detector elements.

In conventional computer tomography devices of this type, having a stationary radiation detector, the number of detector elements in the radiation detector is so low that image reconstruction when using the focus as the projection center would produce an unacceptable image resolution. The measured data for each detector element must be acquired and intermediately stored during the rotation of the radiation source, so that real-time measured data processing is not possible. Even if the hardware outlay were increased, by using a greater number of more narrow detector elements, such a computer tomography device would violate the sampling theorem, given the conventional reconstruction techniques wherein the focus of the radiation source is used as the image projection center, because each detector element would be more narrow than the center-to-center spacing of the detector elements.

SUMMARY OF THE INVENTION

It is an object of the present invention to provide a computer tomography apparatus wherein a rapid image generation is achieved without violating the sampling theorem.

The above object is achieved in accordance with principles of the present invention in a computer tomography apparatus wherein the radiation detector is rotated around an axis separately from the radiation source, simultaneously with the separate rotation of the radiation source. The rotation angle from projection-to-projection is preferably $(m/n) \cdot \Delta$ wherein m and n are integers, with n being the number of revolutions of the radiation source and $\Delta$ being the center-to-center detector element spacing. A decoupling of the scanning grid dimension from the physical detector width occurs at the "detector side" of the structure, so that it is possible to satisfy the sampling theorem. At the same time, image reproduction can be undertaken using the radiation source focus as the projection center, so that real-time measured data processing can be undertaken. In a computer tomography apparatus of the so-called fourth generation, immediate production of images is possible.

DESCRIPTION OF THE DRAWING

The single figure is a schematic end elevational view showing the basic components of a computer tomography apparatus constructed in accordance with the principles of the present invention.

DESCRIPTION OF THE PREFERRED EMBODIMENTS

As shown in the drawing, a computer tomography apparatus constructed in accordance with the principles of the present invention has a penetrating radiation source, such as an x-ray source 2, mounted on a live ring 1. The x-ray source 2 is rotated around an axis 20 by a rotary x-ray source drive 3. The x-ray source 2 emits a fan-shaped x-ray beam 4, which penetrates a slice of an exposure subject 5 from different directions, as the x-ray source 2 is rotated. The radiation attenuated by the exposure subject 5 is received by an annular radiation detector assembly 6, which includes a row of detector elements 7. The center-to-center detector spacing is referenced $\Delta$. The x-ray source is fed by a high voltage supply 8.

Output signals (data) from the detector elements 7 during the revolution of the x-ray source 2 are supplied to a computer 9, which calculates the attenuation values of predetermined picture elements of the examined slice of the exposure subject 5 therefrom, and reproduces a viewable image on a display 10.

The detector elements 7 are attached to a detector ring 11. The detector carrier ring 11 is mounted on a guide carrier ring 13, with the detector carrier ring 11 being rotatable around the axis 20 by means of bearings 12. The rotation is undertaken by a motor 14 via a worm 15 and a gear 16.

The x-ray source 2 has a focus 17. As the focus 17 rotates once around the entire focal circle 18, the detector ring 11 is turned by the fraction m/n of the center-to-center detector spacing $\Delta$. The numbers m and n are integers, and n is the number of revolutions. If m is selected so as to be relatively prime with respect to n, each of the positions of the detector elements will be assumed exactly once in the spacing $\Delta/n$ by different detector elements. If m is greater than one, however, the detector elements will not assume these positions in a naturally ordered sequence. An example is shown below, wherein n=4=number of revolutions of the focus 17.

|       | m = 1 | 2   | 3            |
|-------|-------|-----|--------------|
| k = 0 | 0     | 0   | 0            |
| 1     | 1/4   | 1/2 | 3/4 ≙ 3/4    |
| 2     | 2/4   | 0   | 2/4 ≙ 6/4    |
| 3     | 3/4   | 1/2 | 1/4 ≙ 9/4    |
| 4     | 0     | 0   | 0 ≙ 12/4     |
| 5     | 1/4   | 1/2 | 3/4 ≙ 15/4   |

In the above table of detector elements positions, k is the number of the revolution and the position of the detector element is indicated in units $\Delta$. For m=3, it can be seen that the positions are not assumed in a natural sequence, and additionally are assumed by interchanged detector elements.

Thus, for example, the position ¼ is assumed after three dislocations by the second detector element.

The relationship m=n/2 is of particular practical significance (n must thereby be an even number). If this relationship holds, a detector element is displaced by $\Delta/2$ with each revolution. The relationships $m/n=\frac{1}{3}$ and $m/n=\frac{2}{3}$ can also be of practical interest.

A goal of the invention is to satisfy the sampling theorem at the detector side of the device by decoupling the sampling interval length $\Delta$ from the physical detector element width.

The motion of the focus 17 must ensue synchronously with the rotation of the worm 15 in order to meet the condition of the detector element dislocation being $(m/n) \cdot \Delta$ per focus revolution.

It may also be possible to directly mount the detector ring 11 to bearings at three points, in which case the guide ring 13 would not be needed.

It is also possible that the focal circle 18 may be outside of the ring 11 if, for example, the ring 11 is eccentrically mounted. Another variation is to displace the focus of the radiation source around a ring-shaped stationary anode by electrical or magnetic deflection of the electron beam, thereby dispensing with mechanical motion of the radiation source.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computer tomography apparatus for examining a subject comprising:

a source of penetrating radiation which generates a fan-shaped radiation beam in which an examination subject is disposed;

means for rotating said source of penetrating radiation around an axis so that said examination subject is irradiated from different angular positions;

a radiation detector consisting of a row of individual detector elements disposed to detect radiation from said source attenuated by said examination subject, each detector element generating an electrical signal corresponding to the radiation incident thereon and each angular position of said source of penetrating radiation resulting in an image projection on said radiation detector;

means for rotating said radiation detector around said axis separately from said source of penetrating radiation during irradiation of said examination subject through a rotational angle of $(m/n) \cdot \Delta$ for each projection, wherein m and n are integers, n is the number of revolutions of the source of penetrating radiation, and $\Delta$ is the center-to-center detector element spacing; and means for electronically constructing and displaying an image of a slice of said examination subject contained in said fan-shaped radiation beam from said electrical signals of said detector elements.

2. A computer tomography apparatus as claimed in claim 1, wherein $m=n/2$, and n is an even number.

3. A computer tomography apparatus as claimed in claim 1, wherein $m/n=\frac{1}{3}$.

4. A computer tomography apparatus as claimed in claim 1, wherein $m/n=\frac{2}{3}$.

* * * * *